United States Patent [19]
Senanayake

[11] Patent Number: 5,965,622
[45] Date of Patent: Oct. 12, 1999

[54] DESFORMOTEROL AND PROCESS FOR ITS PREPARATION

[75] Inventor: Chris Hugh Senanayake, Shrewsbury, Mass.

[73] Assignee: Sepracor Inc., Marlborough, Mass.

[21] Appl. No.: 09/103,212

[22] Filed: Jun. 23, 1998

[51] Int. Cl.$^6$ .................................................. A61K 31/135
[52] U.S. Cl. ........................................ 514/653; 564/255
[58] Field of Search ............................ 504/255; 514/653

[56] References Cited

FOREIGN PATENT DOCUMENTS 2 031 407 of 1992 Spain .......................... C07C 231/00

OTHER PUBLICATIONS

Hett, R. et al., "Large–Scale Synthesis of Enantio–and Diastereomerically Pure (R,R)–Formoterol," Organic Process Research & Deveopment, vo. 2, pp. 96–99, 1998.
Hett, R. et al., Enantio–and Diastereoselective Synthesis of all Four Stereoisomers of Formoterol, Tetrahedron Letters, vol. 38, No. 7 pp. 1125–1128, 1997.

Primary Examiner—James H. Reamer
Attorney, Agent, or Firm—Heslin & Rothenberg, P.C.

[57] ABSTRACT

The (R,R)-, (S,S)-, (R,S)-, (R,S)- isomers of 3-amino-4-hydroxy-α-[[[2-(4-methoxyphenyl)-1-methylethyl]amino]methyl]-benzenemethanol (D)

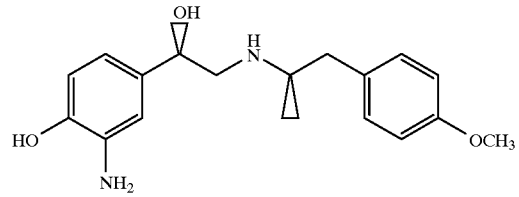

are disclosed, as well as an efficient method for their stereoselective synthesis. A method and composition are also disclosed utilizing desformoterol (D) as a bronchodilator, having high selectivity for $\beta_2$ receptors.

31 Claims, No Drawings

DESFORMOTEROL AND PROCESS FOR ITS PREPARATION

FIELD OF THE INVENTION

The present invention relates to 3-amino-4-hydroxy-α-[[[2-(4-methoxy phenyl)-1-methylethyl]amino]methyl] benzenemethanol, to pharmaceutical compositions thereof and to its use in treating and preventing pulmonary disorders. The invention further relates to optically pure isomers of 3-amino-4-hydroxy-α-[[[2-(4-methoxyphenyl)-1-methylethyl]amino]methyl]-benzenemethanol and a process for their preparation.

BACKGROUND OF THE INVENTION

Formoterol, (+/−)N-[2-hydroxy-5-[1-hydroxy-2 [[2-(p-methoxy phenyl)-2-propyl]amino]ethyl]phenyl]-formamide, is a highly potent and $\beta_2$-selective adrenoceptor agonist having a long lasting bronchodilating effect when inhaled. The structure of formoterol is as shown:

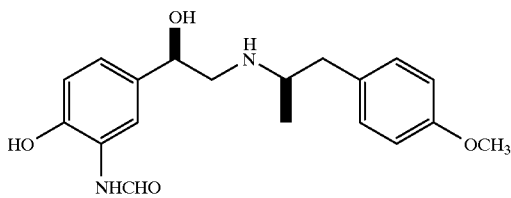

Formoterol has two chiral centers in the molecule, each of which can exist in two possible configurations. This gives rise to four combinations: (R,R), (S,S), (R,S) and (S,R). (R,R) and (S,S) are mirror images of each other and are therefore enantiomers; (R,S) and (S,R) are similarly an enantiomeric pair. The mirror images of (R,R) and (S,S) are not, however, superimposable on (R,S) and (S,R), which are diastereomers. Formoterol is available commercially only as a racemic mixture (R,R) plus (S,S) in a 1:1 ratio, and the generic name formoterol refers to this enantiomeric mixture.

The graphic representations of racemic, ambiscalemic and scalemic or enantiomerically pure compounds used herein are taken from Maehr J. Chem. Ed. 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula for formoterol above reflects the racemic nature of the commercial material, while among the structures below, those having open wedges are intended to encompass both of the pure enantiomers of that pair and those having solid wedges are intended to encompass the single, pure enantiomer having the absolute stereochemistry shown.

| Symbol | Stereochemical Significance |
|---|---|
| Representation of Bonds to Chiral Carbons According to Maehr | |
| ⫽△ | Optically pure - Indeterminate Configuration |
| ⫽▮ | Racemic - but having the relative configuration shown |
| ▼⫽ | Chiral - Absolute Configuration |
| ⌇ | No Stereochemistry Indicated |

The synthesis of the four stereoisomers of formoterol has been reported in the literature. In one method, the (R,R)- and (S,S)- isomers were isolated by stereoselective crystallization of racemic formoterol with optically pure tartaric acid (Murase et al., Chem. Pharm. Bull. 26, 1123–1129 (1978)). In another method, racemic 4-benzyloxy-3-nitrostyrene oxide was coupled with an optically pure (R,R)- or (S,S)-N-(1-phenylethyl)-N-(1-(p-methoxyphenyl)-2-propyl) amine to give a diastereomeric mixture of formoterol precursors, which were then separated by semipreparative HPLC and transformed to the pure formoterol isomers (Trofast et al., Chirality 3, 443–450 (1991)). Both methods suffer from very low yields (<2%) and long synthetic procedures.

3-Amino-4-hydroxy-α-[[[2-(4-methoxyphenyl)-1-methylethyl]amino]methyl]-benzenemethanol (Chem. Abst. Reg. No. 150513-24-9) has been disclosed as an undesired side product in a synthesis of formoterol (Spanish Patent ES 2031407). Its structure is shown below.

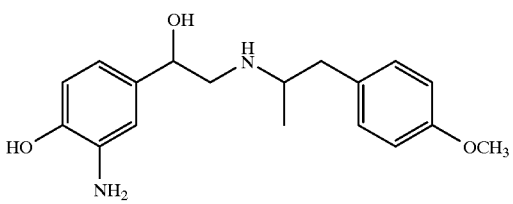

Neither its deliberate synthesis nor its pharmacology has been previously reported.

SUMMARY OF THE INVENTION

It has now been discovered that 3-amino-4-hydroxy-α-[[[2-(4-methoxyphenyl)-1-methylethyl]amino]methyl] benzenemethanol (I) is also a highly selective $\beta_2$-adrenergic receptor agonist. The processes of the invention provide a practical, efficient method for preparing the compound, and also provide a synthesis of all of its four stereoisomers with high optical purity.

The compounds, methods and compositions of the invention relate to 3-amino-4-hydroxy-α-[[[2-(4-methoxyphenyl)-1-methylethyl]amino]methyl] benzenemethanol and to stereoisomers thereof. For simplicity's sake, 3-amino-4-hydroxy-α-[[[2-(4-methoxyphenyl)-1-methylethyl]amino]methyl] benzenemethanol will henceforth be referred to as "desformoterol." Throughout the instant disclosure, when the term is not otherwise modified, "desformoterol" indicates the R,R-isomer, the S,S-isomer, the R,S-isomer, the S,R-isomer or any mixture of these stereoisomers. The term "racemic desformoterol" includes the two possible racemates, one a mixture of the R,R- and the S,S-isomers, and the other, a mixture of the R,S- and the S,R-isomers.

In one aspect, the invention relates to a process for preparing a compound of formula:

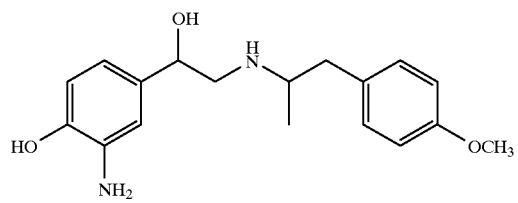

comprising providing a compound of formula;

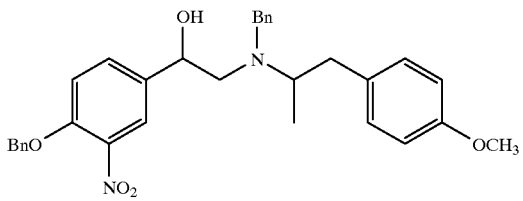

and reducing said compound. The compound of formula

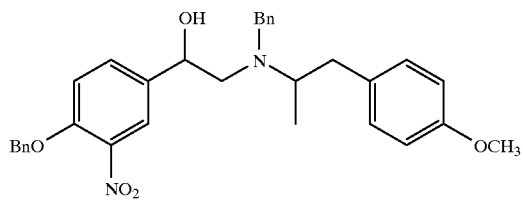

is prepared by reacting a compound of formula

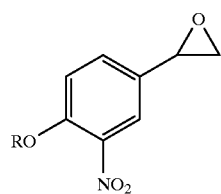

with a compound of formula

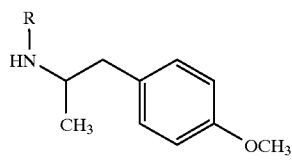

wherein R is benzyl or substituted benzyl.

Similarly, the invention relates to a process for preparing a salt of an optically pure compound of formula:

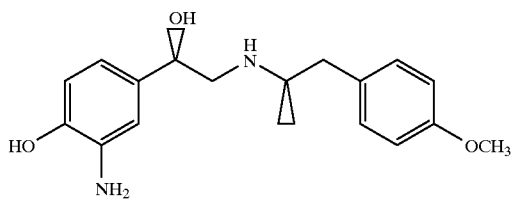

by providing a compound of formula

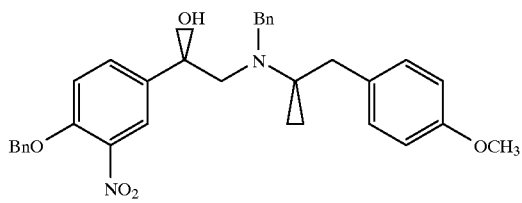

and reducing said compound in the presence of an acid. The compound of formula

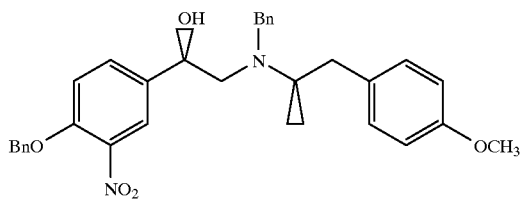

is prepared by reacting a compound of formula

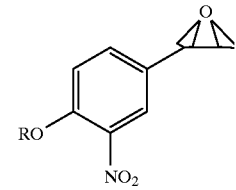

with a compound of formula

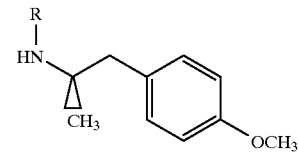

wherein R is benzyl or substituted benzyl.

The term "substituted benzyl" refers to any protecting group for a phenol that contains the benzyl (or phenylmethyl) nucleus substituted with one or more substituents that do not interfere with its function as a protecting group. Suitable substituents include: $C_1$ to $C_6$-alkyl, $C_1$ to $C_6$-alkoxyl, halogen and combinations thereof. In a particular embodiment, R is benzyl, represented herein as Bn.

In the foregoing processes the reducing step is carried out with a source of hydrogen in the presence of a noble metal catalyst. A preferred noble metal catalyst is palladium. It is further preferred that the reducing step be carried out in the presence of tartaric acid in addition to the catalyst. The source of hydrogen may be hydrogen gas or a hydrogen-donating compound such as ammonium formate.

Suitable acid addition salts for the compounds of the present invention include for example, acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. The mandelic acid salt is especially preferred for benzylamine compounds; the tartrate is preferred for desformoterol stereoisomers.

The present invention also includes novel compositions of matter, containing desformoterol, which are useful as bronchodilators for the relief of reversible bronchospasm in patients with obstructive airway disease such as asthma, bronchitis and emphysema.

In one aspect the invention relates to methods of inducing bronchodilation or preventing bronchoconstriction with desformoterol comprising administering to an individual a quantity of desformoterol sufficient to induce bronchodilation or prevent bronchoconstriction. The desformoterol may be administered orally or by subcutaneous injection, intravenous infusion, inhalation, or transdermal delivery. Inhalation is preferred. The amount administered by inhalation is about 1 µg to about 100 µg per day, in single or divided doses.

In another aspect, the invention relates to compositions for oral administration, including syrups and unit dosage forms, such as tablets and capsules, or formulations suitable for administration by inhalation, e.g. solution or suspension in a suitable propellant for use in a metered-dose inhaler or sterile aqueous solution for nebulization. The compositions comprise a pharmaceutically acceptable propellant (for aerosols) or carrier (for inhalation solutions, syrups, tablets and capsules) and desformoterol or a pharmaceutically acceptable salt thereof. A preferred bronchodilator composition is in the form of an aerosol formulation.

DETAILED DESCRIPTION

In one aspect, the present invention relates to a practical and efficient process for the preparation of desformoterol and optically pure isomers. This method is particularly advantageous because it utilizes optically pure precursors that are readily available by simple resolution and asymmetric reduction. Mixtures of enantiomers of desformoterol may be prepared conveniently by starting with materials which are not optically pure.

The overall sequence is set forth in Scheme 1, wherein R has been exemplified as benzyl, represented as Bn. The scheme illustrates the procedure for the synthesis of optically pure products, but the same procedure is useful for preparing mixtures of isomers. The sequence could also be used to produce other intermediates in which R is substituted benzyl by beginning with the appropriate starting material analogous to 2. Brackets indicate intermediates that could be isolated but may not be isolated in the integrated process.

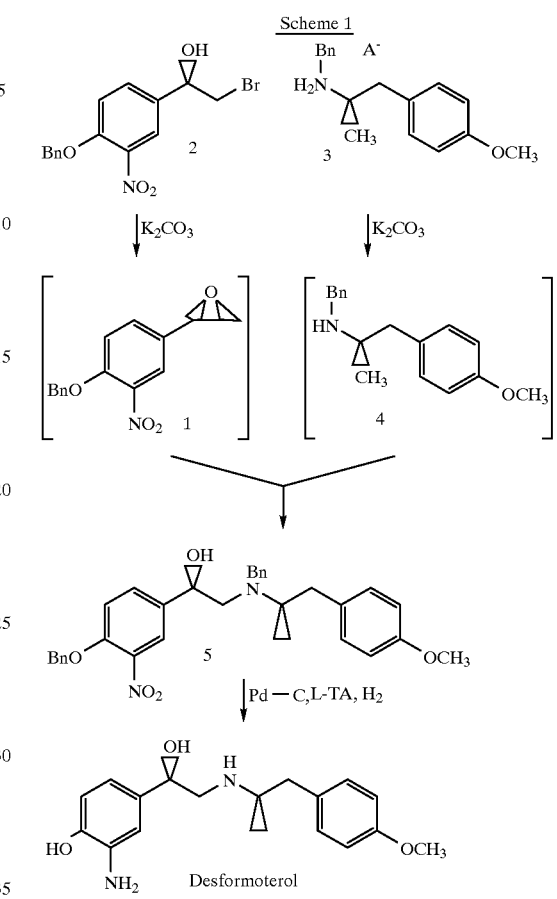

In the process described above, the optically pure 4-methoxy-α-methyl-N-(phenylmethyl)benzene ethanamine, also called 2-N-benzylamino-1-(p-methoxyphenyl)propane 4, is obtained by resolution of the racemic compound with L- or (D)-mandelic acid using a modification of the procedure of Kraft, et al. [*Rec. Trav. Chim. Pays-Bas* 85, 607 (1966)]. The racemic N-benzylamine compound was prepared by the reductive amination of p-methoxyphenylacetone with N-benzylamine under catalytic hydrogenation, but other reductive conditions using methods known in the art could be used. (See, *Houben-Weyl's Methoden der Org. Chem.* Band IV/1c, p427.)

The invention encompasses a process for making optically pure desformoterol from optically pure 4-benzyloxy-3-nitrostyrene oxide 1 comprising the coupling and hydrogenation described above in combination with a method for the preparation of the optically pure styrene oxides. According to this aspect the optically pure styrene oxide is obtained by: (a) reduction of 2'-bromo4-benzyloxy-3-nitroacetophenone with borane stereoselectively in the presence of a chiral oxazaborolidine catalyst to give the corresponding optically active bromohydrin [See Hong, et al., *Tetrahedron Lett.* 35, 6631(1994) and U.S. Pat. No. 5,495,821, the disclosures of which are incorporated herein by reference]; and (b) conversion of the 3-nitro-bromohydrin to the corresponding 4-benzyloxy-3-nitrostyrene oxide 1 with a base.

The optically pure 2-N-benzylamino-1-(p-methoxyphenyl)propane 4 is obtained by resolution of the racemic compound with L- or D-mandelic acid. The resolution of the racemic N-benzylamine compound is performed using one equivalent of L- or D-mandelic acid in an alcohol solvent such as methanol (MeOH). The optically pure benzylamine mandelic acid salt 3 is obtained after four or five crystallizations. The free N-benzylamine compound is then obtained by treating the mandelic acid salt with a base such as aq. NaOH or aq. $Na_2CO_3$ or aq. $NH_3$ in the presence of an inert organic solvent such as t-butyl methyl ether (MTBE) or ethyl acetate (EtOAc) followed by evaporation of the solvent. (R)-2-N-benzylamino-1-(p-methoxyphenyl)propane is obtained from the L-(+)-mandelic acid salt while the (S)-enantiomer is obtained from the D-(−)-mandelic acid salt. From the same lot of racemic N-benzylamine compound, both (R)- and (S)-enantiomer can be obtained by using the appropriate mandelic acid.

The optically pure epoxide 1 is prepared from commercially available 4-benzyloxy-3-nitroacetophenone. Thus, the acetophenone may be brominated with bromine in an inert organic solvent such as $CH_3CN$, MeOH or chloroform to give the α-bromoacetophenone. The bromoacetophenone is then reduced with a borane reducing agent such as $BH_3$.THF or $BH_3.Me_2S$ in the presence of a chiral oxazaborolidine catalyst to give the optically active bromohydrin by extraction from aqueous acid in excellent yield (>98%) and good enantiomeric excess (ee=95%). An example of such a catalyst is cis-(1R,2S)-aminoindanol-B-Me, or AIBMe, which is the product of the reaction between cis-(1R,2S)-aminoindanol and trimethylboroxine, according to the procedure described in U.S. Pat. No. 5,495,821. The bromohydrin can be further enriched to >99.8% ee by crystallization. The absolute configuration of the bromohydrin is determined by the chirality of the oxazaborolidine catalyst. The resulting compound is converted to optically pure 4-benzyloxy-3-nitrostyrene oxide with a base such as aq. NaOH or $K_2CO_3$ in an alcohol solvent or solvent mixture such as MeOH/THF. The epoxide can be isolated by extraction of the reaction mixture with ethyl acetate/water, drying the organic phase and evaporating the solvent.

Epoxide formation from bromohydrin 2 and release of the free base from benzylamine 3 may be accomplished in separate steps or in a single step. The optically pure 2-N-benzylamino-1-(p-methoxyphenyl) propane 4 is reacted with optically pure 4-benzyloxy-1-nitrostyrene oxide 1 without racemization to give an optically pure N,O-dibenzyldesformoterol intermediate 5, and the N,O-dibenzyl groups of the dibenzyl-desformoterol are removed by hydrogenation in the presence of a hydrogenation catalyst, to give optically pure desformoterol. However, since both reactions require a base, a combination of both steps into a one-pot procedure is possible and simplifies the process. Under this scheme, the dibenzyl-desformoterol is obtained directly from the reaction of optically pure 2-N-benzylamino-1-(p-methoxyphenyl) propane 3 with the optically pure 1-(4'-benzyloxy-3'-nitrophenyl)-2-bromoethanol 2 in the presence of a base whereby the epoxide 1 is formed in situ.

The condensation of the N-benzylamine sidechain with the epoxide may be carried out without solvent at temperature in the range of 100–140° C., or in a high boiling inert solvent under reflux. Suitable solvents include toluene, t-butanol, t-amyl alcohol, and methyl isobutylketone (MIBK). The resulting dibenzyldesformoterol 5 can be purified by column chromatography. It can also be used directly without purification for the de-benzylation reaction to form desformoterol.

The dibenzyldesformoterol product is converted by catalytic hydrogenation in the presence of Pd catalyst such as Pd/C directly to desformoterol. The hydrogenolysis is preferably performed on a salt formed from an appropriate organic acid, in an alcohol solvent such as methanol, ethanol, or 2-propanol, at 40–60 psi of hydrogen pressure and at a temperature of 15–30° C. for 2–15 hours.

The resulting desformoterol acid salt is then isolated by removing the solvent after filtration to remove the catalyst. The acid may be present in any ratio, but one equivalent is optimal with non-volatile acids, in that the salt is directly isolated from the reaction. Employing a ratio greater than one is generally unnecessary and a ratio less than one results in slower hydrogenolysis and a need to further manipulate the product to obtain either the free base or a pure salt.

It has been observed that the stability of desformoterol can vary according to conditions. The compound exhibits maximum stability in an environment maintained at a pH of 2.

Binding studies of desformoterol and individual diasteromers have shown that the racemate and the R,R stereoisomer are highly selective β-adrenergic receptor agonists. The four isomers of desformoterol, (R,R)-, (S,S)-, (R,S)-, and (S,R)-, and a 1:1 mixture of the (R,R)- and the (S,S)-enantiomers, were screened, in duplicate, at three concentrations ($10^{-9}$, $10^{-7}$, $10^{-5}$ M) for binding to human $β_1$ and $β_2$-adrenergetic receptors. The compounds were then tested at ten concentrations in duplicate in order to obtain full competition curves. Reference compounds were simultaneously tested at eight concentrations. $IC_{50}$ values (concentration required to inhibit 50% of specific binding) were then determined by nonlinear regression analysis. Results are tabulated below.

TABLE 1

| COMPOUND | $IC_{50}$ (nM) | | |
|---|---|---|---|
| | $β_1$ | $β_2$ | $β_1/β_2$ Selectivity |
| (R,R)-Desformoterol | 3,180 | 35.6 | 89 |
| Atenolol | 1,200 | — | — |
| ICI 118551 | — | 2.5 | — |

(R,R)-desformoterol displayed significant binding primarily at the $β_2$-site and its selectivity ($β_1/β_2$) for the $β_2$-receptor was approximately 89-fold.

TABLE 2

| COMPOUND | $IC_{50}$ (nM) | | |
|---|---|---|---|
| | $β_1$ | $β_2$ | $β_1/β_2$ Selectivity |
| (R,S)-Desformoterol | 1,790 | 3,140 | <1 |
| (S,R)-Desformoterol | — | 1,890 | — |
| Atenolol | 1,430 | — | — |
| ICI 118551 | — | 2.4 | — |

Neither (R,S)- nor (S,R)-desformoterol showed high affinity for the $β_1$ receptor. The binding of (R,S)-desformoterol was comparable to that of atenolol at the $β_1$-site, and an $IC_{50}$ was not determined for (S,R)-desformoterol because only 22% inhibition was attained at $10^{-5}$ M.

TABLE 3

| COMPOUND | IC$_{50}$ (nM) | | | |
|---|---|---|---|---|
| | $\beta_1$ | $\beta_2$ | $\beta_1/\beta_2$ Selectivity | |
| (R,R)-/(S,S)-Racemate of Desformoterol | 5,142 | 81.3 | 63 | |
| (S,S)-Desformoterol | 64,710 | >10,000 | <6 | |
| Atenolol | 1,300 | — | — | |
| ICI 118551 | — | 1.9 | — | |

Not surprisingly, the (R,R)/(S,S) racemate of desformoterol displayed significant binding only at the $\beta_2$-site, since it is a mixture of equal parts of the (R,R)- and (S,S)-enantiomers, and (S,S)-desformoterol lacked affinity for both $\beta$-adrenergic sites.

The present invention also encompasses a method of inducing a bronchodilation effect or preventing bronchoconstriction which comprises administering to a human in need of bronchodilation an amount of desformoterol or a pharmaceutically acceptable salt thereof sufficient to alleviate bronchospasms. Inducing bronchodilation and preventing bronchoconstriction provide relief from the symptoms associated with obstructive airway diseases, e.g., asthma or chronic obstructive pulmonary disease (COPD) which include but are not limited to respiratory distress, wheezing, coughing, shortness of breath, tightness or pressure in the chest and the like.

The present invention additionally encompasses a pharmaceutical composition for the treatment of a patient in need of bronchodilating therapy which comprises desformoterol or a pharmaceutically acceptable salt thereof. The desformoterol may be a single optically pure stereoisomer of a mixture thereof. The term "optically pure stereoisomer" as used herein means that the composition contains at least about 90% by weight of a specific stereoisomer of desformoterol, that is, one of (R,R), (S,S), (R,S) or (S,R), and 10% or less by weight of any combination of other stereoisomers of desformoterol. In a more preferred embodiment the composition contains at least 99% by weight of a single stereoisomer of desformoterol and 1% or less of other stereoisomers. In the most preferred embodiment the composition contains greater than 99% by weight of a single stereoisomer of desformoterol and less than 1% by weight of other stereoisomers.

The magnitude of a prophylactic or therapeutic dose of desformoterol in the acute or chronic management of disease will vary with the severity of the condition to be treated, and the route of administration. The dose, and perhaps the dose frequency, will also vary according to the age, body weight, and response of the individual patient. In general, the total daily dose ranges when administered by inhalation, for the conditions described herein, is from about 1 $\mu$g to about 100 $\mu$g, in single or divided doses. Preferably, a daily dose range should be between about 6 $\mu$g to about 25 $\mu$g, in single or divided doses, in from two to four divided doses. In managing the patient, the therapy should be initiated at a lower dose, perhaps about 3 $\mu$g to about 12 $\mu$g, and increased up to about 2×12 $\mu$g or higher depending on the patient's global response. When administered orally, preferably as a tablet, the preferred dose range is from 0.1 to 1.0 mg per day. It is further recommended that children, and patients over 65 years, and those with impaired renal, or hepatic function, initially receive low doses, and that they be titrated based on individual responses and blood levels. It may be necessary to use dosages outside these ranges in some cases as will be apparent to those skilled in the art. Further, it is noted that the clinician or treating physician would know how and when to interrupt, adjust, or terminate therapy in conjunction with individual patient response. The terms "an amount sufficient to alleviate bronchospasms," "an amount sufficient to prevent bronchoconstruction" and "a therapeutically effective amount" are encompassed by the above-described dosage amounts and dose frequency schedule.

The pharmaceutical compositions of the present invention comprise as the active ingredient desformoterol thereof or a pharmaceutically acceptable salt thereof, and may also contain a pharmaceutically acceptable carrier, and optionally, other therapeutic ingredients. The term "pharmaceutically acceptable salts" or "a pharmaceutically acceptable salt thereof" refer to salts prepared from pharmaceutically acceptable nontoxic acids including inorganic acids and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. The tartaric acid salt is particularly preferred.

Preferred unit dosage formulations are those containing an effective dose, as recited, or an appropriate fraction thereof, of the active ingredients particularly mentioned above. The formulations of this invention may include other agents conventional in the art having regard to the type of formulation in question. For example, formulations for oral administration may include carriers such as starches, sugars, microcrystalline cellulose, diluents, granulating agents, flavoring agents and the like. The compositions include formulations suitable for oral, rectal and parenteral administration (including subcutaneous, transdermal, intramuscular, and intravenous) and inhalation.

Any suitable route of administration may be employed for providing the patient with an effective dosage of desformoterol. For example, oral, rectal, parenteral (subcutaneous, intramuscular, intravenous), transdermal, and like forms of administration may be employed. Dosage forms include tablets, troches, dispersions, suspensions, solutions, capsules, patches, syrups, and the like. Oral and parenteral sustained release dosage forms may also be used.

Oral syrups, as well as other oral liquid formulations, are well known to those skilled in the art, and general methods for preparing them are found in any standard pharmacy school textbook, for example *Remington: The Science and Practice of Pharmacy.* Chapter 86 of the 19th edition of Remington entitled "Solutions, Emulsions, Suspensions and Extracts" describes in complete detail the preparation of syrups (pages 1503–1505) and other oral liquids. Similarly, sustained release formulation is well known in the art, and Chapter 94 of the same reference, entitled "Sustained-Release Drug Delivery Systems," describes the more common types of oral and parenteral sustained-release dosage forms (pages 1660–1675.) The relevant disclosure, Chapters 84 and 96, is incorporated herein by reference.

The most preferred route of administration of the present invention is inhalation. Formulations suitable for inhalation include sterile solutions for nebulization comprising a therapeutically effective amount of desformoterol, or a pharmaceutically acceptable salt thereof, dissolved in aqueous saline solution and optionally containing a preservative such as benzalkonium chloride or chlorobutanol, and aerosol formulations comprising a therapeutically effective amount of desformoterol, or a pharmaceutically acceptable salt thereof, dissolved or suspended in an appropriate propellant (e.g., HFA-134a, HFA-227, or a mixture thereof, or a chlorofluorocarbon propellant such as a mixture of Propellants 11, 12 and/or 114) optionally containing a surfactant. Aerosols may be conveniently presented in unit dosage form and prepared by any of the methods well-known in the art of pharmacy. The preparation of a particularly desirable aerosol formulation is described in European Patent No. 556239, the disclosure of which is incorporated herein by reference. Also suitable are dry powder formulations comprising a therapeutically effective amount of desformoterol, or a pharmaceutically acceptable salt thereof, blended with an appropriate carrier and adapted for use in connection with a dry-powder inhaler.

The invention is further defined by reference to the following examples describing in detail the preparation of the compounds, the pharmacological characterization thereof, and the preparation of compositions of the present invention. It will be apparent to those skilled in the art, that many modifications, both to materials, and methods, may be practiced without departing from this invention.

EXAMPLE 1

2-Bromo-4'-benzyloxy-3'-nitroacetophenone

A 5-liter flask was charged with 300 g (1.1 mol) of 4-benzyloxy-3-nitroacetophenone and 3 liters of acetonitrile. The mixture was heated to 50° C. to form a clear solution, and 180 g of bromine (1.6 mol) was added in one portion. The reaction was stirred at 50° for 15–25 minutes, during which time the deep red color changed to pale orange and TLC (ethyl acetate/hexane 3:7) showed no remaining starting material. Without heating, 200 to 300 mL of acetonitrile, along with the byproduct hydrogen bromide, were distilled from the reaction under vacuum. During the course of the distillation, the temperature dropped to about 15° and the product precipitated as a yellow solid. The reaction was stirred at 0–5° for two hours and the product was filtered off and washed with acetonitrile. The resulting 2-bromo 4'-benzyloxy-3'-nitroacetophenone was dried in vacuum to yield 242 g (63%) of an off-white solid having a melting point of 136° C.

EXAMPLE 2

R-2-Bromo-1-((4-benzyloxy)-3-nitrophenyl) ethanol (2)

Cis-(1R,2S)-aminoindanol (0.2 eq.)was reacted with trimethylboroxine (0.07 eq.) in toluene to give oxazaborolidine. After azeotropic removal of methaneboronic acid, THF and borane (0.2 eq.) were added followed by simultaneous addition of more borane (0.7 eq.) and a solution of bromoketone 2-bromo 4'-benzyloxy-3'-nitroacetophenone (1 eq.) in tetrahydrofuran at −15° C. The product (R)-bromohydrin was isolated by extraction from aqueous acid in >98% yield (ee=95%).

EXAMPLE 3

4-Benzyloxy-3-nitrostyrene oxide (1)

If it is desired to isolate the epoxide, as opposed to generating it in situ in the next step, the following procedure may be used: A solution of the R-enantiomer of 2 (16.0 g, 45 mmol, ee=99.9%) in THF (100 mL) and methanol (100 mL) was stirred in the presence of potassium carbonate (8.3 g) for 2 hours. The reaction mixture was concentrated and then extracted with ethyl acetate (200 mL) and water (100 mL). The organic layer was dried over $Na_2SO_4$, filtered and concentrated leaving 12.0 g (97%) of 1 as an orange solid.

EXAMPLE 4

(R,R)-2-Benzyloxy-5-[1-hydroxy-2-[[2-(4-methoxyphenyl)-1-methylethyl]amino]ethyl]- 1-nitrobenzene (5)

Epoxide 1 (10.6 g, 39 mmol) was reacted with the R-enantiomer of benzylamine 4 (10.0 g, 30 mmol) under argon at 90° C. for 15 hours. The reaction mixture was purified by column chromatography using EtOAc/hexanes (1:2) to give 15 g of 5 as an orange oil in 73% yield.

EXAMPLE 5

(R,R)-3-amino-4-hydroxy-α-[[[2-(4-methoxyphenyl)-1-methylethyl]amino]methyl]-benzenemethanol (R,R)-Desformoterol The R,R-enantiomer of dibenzyldesformoterol 5 (6.9 g, 13 mmol) was reacted with L-tartaric acid (2.0 g, 13 mmol) in MeOH (5 mL). The mixture was heated to 60° C. and a clear solution was obtained. The solution was concentrated to dryness to leave 9.0 g of the tartrate salt of the R,R-enantiomer of 5 as a yellow powder. This material (2.2 g) was hydrogenated at 50 psi in 30 mL MeOH in the presence of Pd-C (Degussa type NE/W, 10% Pd, 0.4 g). The reaction mixture was filtered through Celite, washed with 60 mL $CH_3CN$ and concentrated to dryness leaving 1.0 g (75%) of (R,R)-desformoterol-L-tartrate as an off-white powder.

EXAMPLE 6

4-Methoxy-α-methyl-N-(phenylmethyl)benzene ethaneamine L-mandelic acid salt (3)

To 800 mL of methanol were added 328 g of 4-methoxyphenylacetone (2 mol) and 214 g of N-benzylamine (2 mol). The imine formation was exothermic and the solution warmed to 45° C. After reaction was complete, the solution was hydrogenated at 50 psi for 6–8 hours in the presence of 3.3 g of 5% platinum on carbon catalyst. When the hydrogen uptake had stopped, the reaction was filtered through diatomaceous earth, and the filter cake was washed with 200 mL of methanol. The combined filtrates were placed in a 6-liter flask and diluted with 4.2 liters of methanol. (S)-L-Mandelic acid (304 g, 2 mol) was added and the mixture heated with stirring to reflux to obtain a clear solution. The solution was cooled to room temperature, stirred at room temperature for two hours and the mandelic acid salt filtered off. The recrystallization was repeated three times to obtain 60–70 g of the mandelic acid salt of the benzyl amine having an isomeric purity greater than 99.8% and a melting point of 164° C.

EXAMPLE 7

Formula for Oral Inhalation

| Formula | Quantity contained in Each Metered Dose Dispenser |
|---|---|
| (R,R,)-desformoterol tartrate | 1.8 mg |
| trichloromonofluoromethane | 5.16 g |
| dichlorodifluoromethane | 5.16 g |
| sorbitan trioleate | 0.105 g |

The metered dose dispenser contains micronized (R,R)-desformoterol tartrate in suspension. Each actuation delivers 6μ of (R,R)-desformoterol tartrate from the mouthpiece. Each canister provides about 300 inhalations.

EXAMPLE 8

Oral Formulation

| | Quantity per Tablet (mg.) | |
|---|---|---|
| Formula | A | B |
| (R,R)-desformoterol tartrate | 0.12 | 0.25 |
| Lactose | 41.38 | 41.25 |
| Cornstarch | 3.0 | 3.0 |
| Water (per thousand Tablets)* | 30.0 ml | 30.0 ml |
| Cornstarch | 5.00 | 5.00 |
| Magnesium Stearate | 0.50 | 0.50 |
| | 50.00 | 50.00 |

*The water evaporates during manufacture.

The desformoterol is mixed with the lactose until a uniform blend is formed. The smaller quantity of cornstarch is blended with the water to form a cornstarch paste. The paste is then mixed with the lactose blend until a uniform wet mass is formed. The remaining cornstarch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine, using ¼ mesh stainless steel screen. The magnesium stearate is then blended and the resulting mixture is compressed into tablets of desired shape, thickness, hardness and disintegration.

I claim:

1. A process for preparing a compound of formula

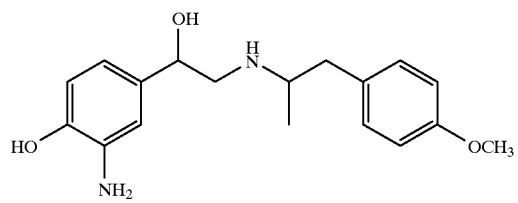

comprising the sequential steps of:

(a) providing a compound of formula;

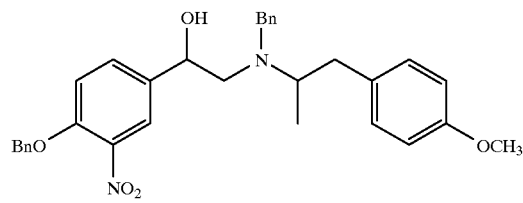

and (b) reducing said compound.

2. A process according to claim 1, wherein the compound of formula:

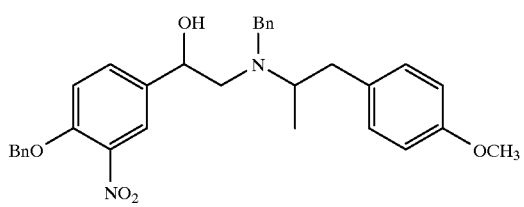

is prepared by reacting a compound of formula

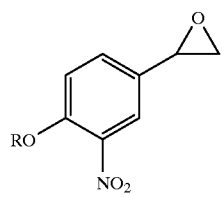

with a compound of formula

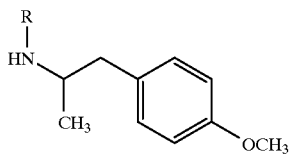

wherein R is benzyl or substituted benzyl.

3. A process for preparing a salt of a compound of formula

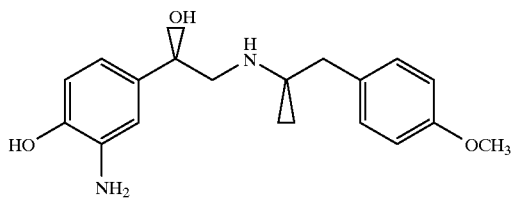

comprising the sequential steps of:

(a) providing a compound of formula;

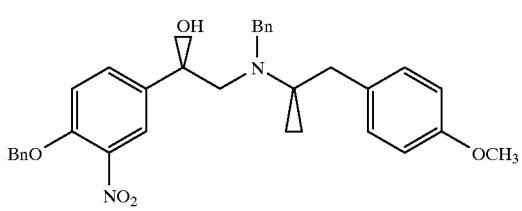

and (b) reducing said compound in the presence of an acid.

4. A process according to claim 3, wherein the compound of formula

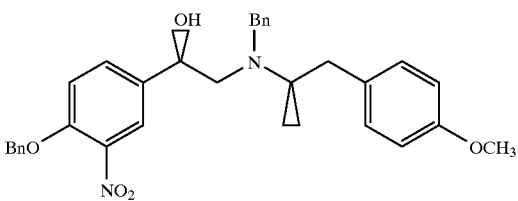

is prepared by reacting a compound of formula

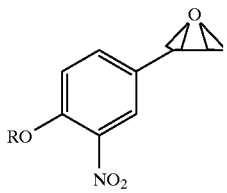

with a compound of formula

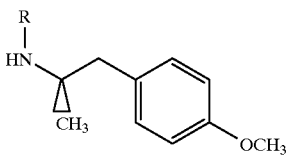

wherein R is benzyl or substituted benzyl.

5. A process according to claim 1 or 3, wherein said reducing step is carried out with a source of hydrogen in the presence of a noble metal catalyst.

6. A process according to claim 5, wherein said noble metal catalyst is palladium.

7. A process according to claim 3, wherein said salt is a tartrate salt, and wherein said reducing step is carried out with a source of hydrogen in the presence of a noble metal catalyst and tartaric acid.

8. A process according to claim 3 wherein said compound of formula

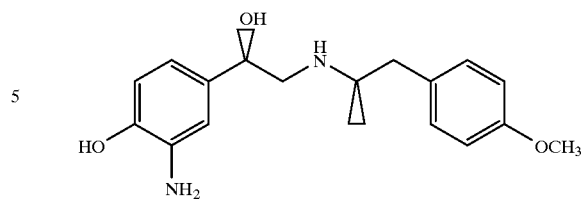

is of the R,R configuration.

9. A process according to claim 3 wherein said compound of formula

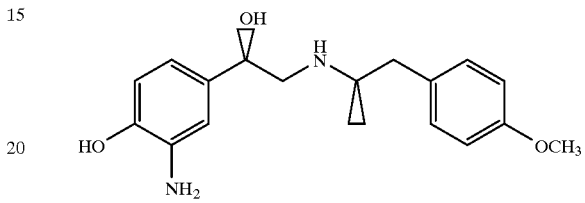

is of the S,S configuration.

10. A process according to claim 3 wherein said compound of formula

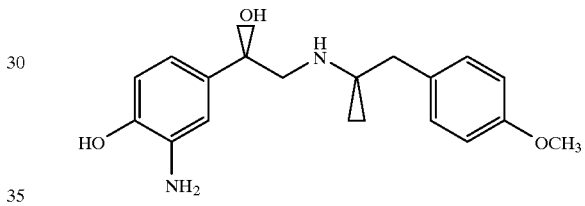

is of the R,S configuration.

11. A process according to claim 3 wherein said compound of formula

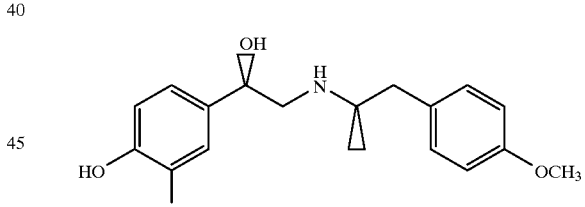

is of the S,R configuration.

12. A method of inducing bronchodilation or preventing bronchoconstriction comprising administering to an individual a therapeutically effective quantity of desformoterol, or a pharmaceutically acceptable salt thereof.

13. The method of claim 12 wherein desformoterol is administered orally or by subcutaneous injection, intravenous infusion, inhalation, or transdermal delivery.

14. A method according to claim 13 wherein desformoterol is administered orally.

15. A method according to claim 13, wherein said desformoterol is administered by inhalation.

16. The method according to claim 15, wherein the amount administered by inhalation is about 1 $\mu$g to about 100 $\mu$g per day.

17. The method of claim 12, wherein racemic desformoterol, or a pharmaceutically acceptable salt thereof, is administered.

18. The method of claim 12, wherein R,R-desformoterol, or a pharmaceutically acceptable salt thereof, is administered.

19. The method of claim 12, wherein R,S-desformoterol, or a pharmaceutically acceptable salt thereof, is administered.

20. A pharmaceutical composition comprising a pharmaceutically acceptable carrier and desformoterol, or a pharmaceutically suitable salt thereof.

21. A pharmaceutical composition according to claim 20 comprising racemic desformoterol, or a pharmaceutically suitable salt thereof, and a pharmaceutically acceptable carrier.

22. A pharmaceutical composition according to claim 20 comprising (R,R)-desformoterol, or a pharmaceutically suitable salt thereof, and a pharmaceutically acceptable carrier.

23. A pharmaceutical composition according to claim 20 in the form of an aerosol formulation, wherein said pharmaceutically acceptable carrier comprises a propellant.

24. A pharmaceutical composition according to claim 20 for oral administration.

25. A pharmaceutical composition according to claim 24 in the form of a syrup.

26. A pharmaceutical composition according to claim 24 in the form of a tablet or a capsule.

27. A pharmaceutical composition according to claim 26 in sustained release form.

28. R,R-desformoterol or a pharmaceutically acceptable salt.

29. S,S-desformoterol or a pharmaceutically acceptable salt.

30. R,S-desformoterol or a pharmaceutically acceptable salt.

31. S,R-desformoterol or a pharmaceutically acceptable salt.

* * * * *

UNITED STATES PATENT AND TRADEMARK OFFICE
CERTIFICATE OF CORRECTION

PATENT NO. : 5,965,622

DATED : October 12, 1999

INVENTOR(S) : Chris Hugh Senanayake

It is certified that error appears in the above-identified patent and that said Letters Patent is hereby corrected as shown below:

IN THE SPECIFICATION:

Col. 6, line 5, Scheme 1, after $H_2N$ insert --+--.

Signed and Sealed this

Second Day of May, 2000

Attest:

Q. TODD DICKINSON

*Attesting Officer*        *Director of Patents and Trademarks*